United States Patent
Bennett et al.

(10) Patent No.: US 12,251,152 B2
(45) Date of Patent: Mar. 18, 2025

(54) CERAMIC APPLICATOR FOR TRANSCUTANEOUS DELIVERY OF ENERGY

(71) Applicant: Solta Medical Ireland Limited, Dublin (IE)

(72) Inventors: Frederick Jay Bennett, Bellevue, WA (US); Craig Robert Bockenstedt, Bothell, WA (US)

(73) Assignee: Solta Medical Ireland Limited, Dublin (IE)

( * ) Notice: Subject to any disclaimer, the term of this patent is extended or adjusted under 35 U.S.C. 154(b) by 532 days.

(21) Appl. No.: 17/299,578

(22) PCT Filed: Dec. 5, 2019

(86) PCT No.: PCT/EP2019/083788
§ 371 (c)(1),
(2) Date: Jun. 3, 2021

(87) PCT Pub. No.: WO2020/120274
PCT Pub. Date: Jun. 18, 2020

(65) Prior Publication Data
US 2022/0022937 A1  Jan. 27, 2022

Related U.S. Application Data

(60) Provisional application No. 62/777,540, filed on Dec. 10, 2018.

(51) Int. Cl.
*A61B 18/14* (2006.01)
*A61B 18/00* (2006.01)
*A61B 18/12* (2006.01)

(52) U.S. Cl.
CPC .... *A61B 18/14* (2013.01); *A61B 2018/00095* (2013.01); *A61B 2018/0047* (2013.01); *A61B 18/1206* (2013.01); *A61B 2018/142* (2013.01)

(58) Field of Classification Search
CPC .............. A61B 18/148; A61B 18/1482; A61B 18/1485; A61B 18/14; A61B 18/1206;
(Continued)

(56) References Cited

U.S. PATENT DOCUMENTS 4,232,676 A * 11/1980 Herczog ................. A61B 18/14
606/50
5,324,289 A *  6/1994 Eggers ............... A61B 18/1206
606/49
(Continued)

FOREIGN PATENT DOCUMENTS

| CN | 101351162 A | 1/2009 |
| JP | 5-33737 U | 5/1993 |

(Continued)

OTHER PUBLICATIONS

The International Bureau of WIPO, International Preliminary Report on Patentability issued Jun. 8, 2021 in International Application No. PCT/EP2019/083788.

(Continued)

*Primary Examiner* — Michael F Peffley
(74) *Attorney, Agent, or Firm* — Thompson Hine LLP

(57) ABSTRACT

Structures for a bidirectional switch and methods of forming such structures. A substrate contact is formed in a trench defined in a substrate. A substrate includes a trench and a substrate contact in the trench. A bidirectional switch, which is on the substrate, includes a first source/drain electrode, a second source/drain electrode, an extension region between the first source/drain electrode and the second source/drain electrode, and a gate structure. A substrate-bias switch, which is on the substrate, includes a gate structure, a first source/drain electrode coupled to the substrate contact, a second source/drain electrode coupled to the first source/drain electrode of the bidirectional switch, and an extension
(Continued)

region laterally between the gate structure and the first source/drain electrode.

24 Claims, 4 Drawing Sheets

(58) Field of Classification Search
CPC .... A61B 2018/1405; A61B 2018/1467; A61B 2018/147; A61B 2018/1495; A61B 2018/00059; A61B 2018/00083; A61B 2018/00101; A61B 2018/00095; A61B 2018/0047; A61B 2018/142
See application file for complete search history.

(56) References Cited

U.S. PATENT DOCUMENTS

| | | | |
|---|---|---|---|
| 6,413,255 | B1 | 7/2002 | Stern |
| 6,855,145 | B2 * | 2/2005 | Ciarrocca ........ A61B 18/1402 606/41 |
| 7,033,354 | B2 * | 4/2006 | Keppel ............... A61B 18/14 606/41 |
| 7,115,123 | B2 | 10/2006 | Knowlton et al. |
| 7,452,358 | B2 | 11/2008 | Stern et al. |
| 8,685,017 | B2 | 4/2014 | Stern et al. |
| 8,702,691 | B2 | 4/2014 | Weber et al. |
| 11,504,182 | B2 * | 11/2022 | Woloszko ............. A61B 18/16 |
| 2002/0052600 | A1 * | 5/2002 | Davison ............ A61B 18/1482 604/35 |
| 2004/0186535 | A1 | 9/2004 | Knowlton |
| 2007/0088413 | A1 | 4/2007 | Weber et al. |
| 2008/0027428 | A1 | 1/2008 | Palanker et al. |
| 2010/0179531 | A1 | 7/2010 | Nebrigic et al. |
| 2015/0201993 | A1 * | 7/2015 | Schomacker ........... A61N 1/28 606/41 |

FOREIGN PATENT DOCUMENTS

| | | |
|---|---|---|
| JP | 2002537939 A | 11/2002 |
| JP | 2005512671 A | 5/2005 |
| JP | 2006521889 A | 9/2006 |
| JP | 2009254651 A | 11/2009 |
| JP | 2012196340 A | 10/2012 |
| KR | 10-2005-0114676 A | 12/2005 |
| WO | 200053112 A1 | 9/2000 |
| WO | 2003053266 A2 | 7/2003 |
| WO | 2004090939 A2 | 10/2004 |
| WO | 2018146729 A1 | 8/2018 |

OTHER PUBLICATIONS

Taiwan Intellectual Property Office, Examination Report issued in Taiwanese Patent Application Serial No. 108144514 on Jan. 5, 2023, 16 pages.
European Patent Office, International Search Report and Written Opinion issued Mar. 24, 2020 in PCT/EP2019/083788.
China National Intellectual Property Administration, First Office Action and Search Report issued in Patent Application Serial No. 201980081238.2 on Dec. 27, 2023; 7 pages.
Taiwan Intellectual Property Office; Notice of Allowance issued in Taiwanese Patent Application Serial No. 108144514 on Aug. 7, 2023; 3 pages.
Japanese Patent Office, Notice of Reasons for Rejection issued in Patent Application Serial No. 2021-531990 on Sep. 8, 2023; 10 pages.
Japanese Patent Office, Notice of Reasons for Rejection issued in Patent Application Serial No. 2021-531990 on Feb. 28, 2024; 12 pages.
European Patent Office, Communication pursuant to Article 94(3) EPC issued in European patent application No. 19817631.5 on May 13, 2024; 4 pages.
Australian Intellectual Property Office, Examination Report No. 1 issued in Australian Patent Application No. 2019400030 on Jun. 13, 2024; 3 pages.
Mexican Intellectual Property Office, First Office Action issued in Mexican Patent Application No. MX/a/2021/006845 on Jun. 21, 2024; 10 pages.
Chinese Intellectual Property Office, Second Office Action issued in Chinese Patent Application No. 201980081238.2 on Jun. 22, 2024; 15 pages.
Australian Intellectual Property Office, Notice of Acceptance for Patent Application issued in Australian Patent Application No. 2019400030 on Sep. 2, 2024; 3 pages.
English translation of Japanese Patent Application No. 2021-531990, published as JP5-33737U on May 7, 1993; 9 pages.
Mexican Intellectual Property Office, Second Office Action issued in Mexican Patent Application No. MX/a/2021/006845 on Sep. 5, 2024; 12 pages.
Korean Intellectual Property Office, Notice of Preliminary Rejection issued in Korean Patent Application No. 10-2021-7017382 on Oct. 21, 2024; 11 pages.
Japanese Patent Office, Final Office Action issued in Japanese Patent Application No. 2021-531990 on Nov. 1, 2024; 8 pages.
Hashimoto, Kaoru, "Materials for Ceramic Substrates/Boards," Purinto Kairo Gijutsu Binran; Printed Circuit Technology Handbook; Third Edition, May 30, 2006; pp. 1018-1034.
China National Intellectual Property Administration, Rejection Decision and Search Report issued in Chinese Patent Application No. 201980081238.2 on Jan. 21, 2025; 24 pages.

* cited by examiner

CERAMIC APPLICATOR FOR TRANSCUTANEOUS DELIVERY OF ENERGY

FIELD OF THE INVENTION

The invention generally relates to energy delivery devices and methods of treating tissue with high-frequency energy.

BACKGROUND

Certain types of energy delivery devices are capable of treating a patient's tissue with electromagnetic energy. These energy delivery devices, which emit electromagnetic energy in different regions of the electromagnetic spectrum for tissue treatment, may be used to treat a multitude of diverse skin conditions. For example, the energy delivery device may non-ablatively and non-invasively treat a skin condition or other type of tissue condition.

One variety of these energy delivery devices emits high-frequency electromagnetic energy in the radio-frequency (RF) band of the electromagnetic spectrum. The high-frequency energy may be used to treat skin tissue by passing high-frequency energy through a surface of the skin, while actively cooling the skin to prevent damage to the skin's epidermal layer closer to the skin surface. The high-frequency energy heats tissue beneath the epidermis to a temperature sufficient to denature collagen, which causes the collagen to contract and shrink and, thereby, tighten the tissue. Treatment with high-frequency energy also causes a mild inflammation. The inflammatory response of the tissue causes new collagen to be generated over time (between three days and six months following treatment), which results in further tissue contraction.

Typically, energy delivery devices include a treatment tip that is placed in contact with, or proximate to, the patient's skin surface and that emits electromagnetic energy that penetrates through the skin surface and into the tissue beneath the skin surface. The non-patient side of the energy delivery device may include a component, such as an applicator including an electrode, for supplying high-frequency energy to the patient's tissue. Traditional applicators include flexible polymeric films upon which an electrode is deposited. The polymeric films, however, suffer from issues of material obsolescence because they often do not enjoy widespread adoption for other applications.

Although conventional applicators for delivering high-frequency energy have proven adequate for their intended purpose, what is needed therefore are improved energy delivery devices for delivering high-frequency energy and improved methods of delivering high-frequency energy.

SUMMARY

In an embodiment, an energy delivery device includes an applicator having an electrode and a substrate of ceramic material. The substrate includes a first surface, a second surface opposite to the first surface, and outer edges arranged between the first surface and the second surface. Additionally, the substrate has a thickness between the first surface and the second surface that varies as a function of position relative to the outer edges.

In another embodiment, an energy delivery device includes an applicator having an electrode and a substrate of ceramic material. The substrate includes a first surface, a second surface opposite to the first surface, and outer edges arranged between the first surface and the second surface. Additionally, the substrate has a thickness between the first surface and the second surface that varies symmetrically about an imaginary centerline extending normal to a major dimension of the first surface and the second surface.

In another embodiment, a method of delivering high-frequency energy is provided. The method includes transferring the high-frequency energy from an electrode through a substrate to treat tissue proximate to the electrode with a current density that is smaller near outer edges of the electrode than inward from the outer edges. The substrate has a thickness that varies as a function of position relative to a plurality of outer edges of the substrate, and the thickness of the substrate is largest near the outer edges.

This summary is provided to introduce a selection of concepts in a simplified form that are further described below in the detailed description. This summary is not intended to identify key features or essential features of the claimed subject matter, nor is it intended to be used in isolation as an aid in determining the scope of the claimed subject matter.

BRIEF DESCRIPTION OF THE DRAWINGS

The accompanying drawings, which are incorporated in and constitute a part of this specification and in which like reference numerals refer to like features, illustrate embodiments of the invention and, together with a general description of the invention given above and the detailed description of the embodiments given below, serve to explain the principles of the invention.

DETAILED DESCRIPTION

Figure 1:
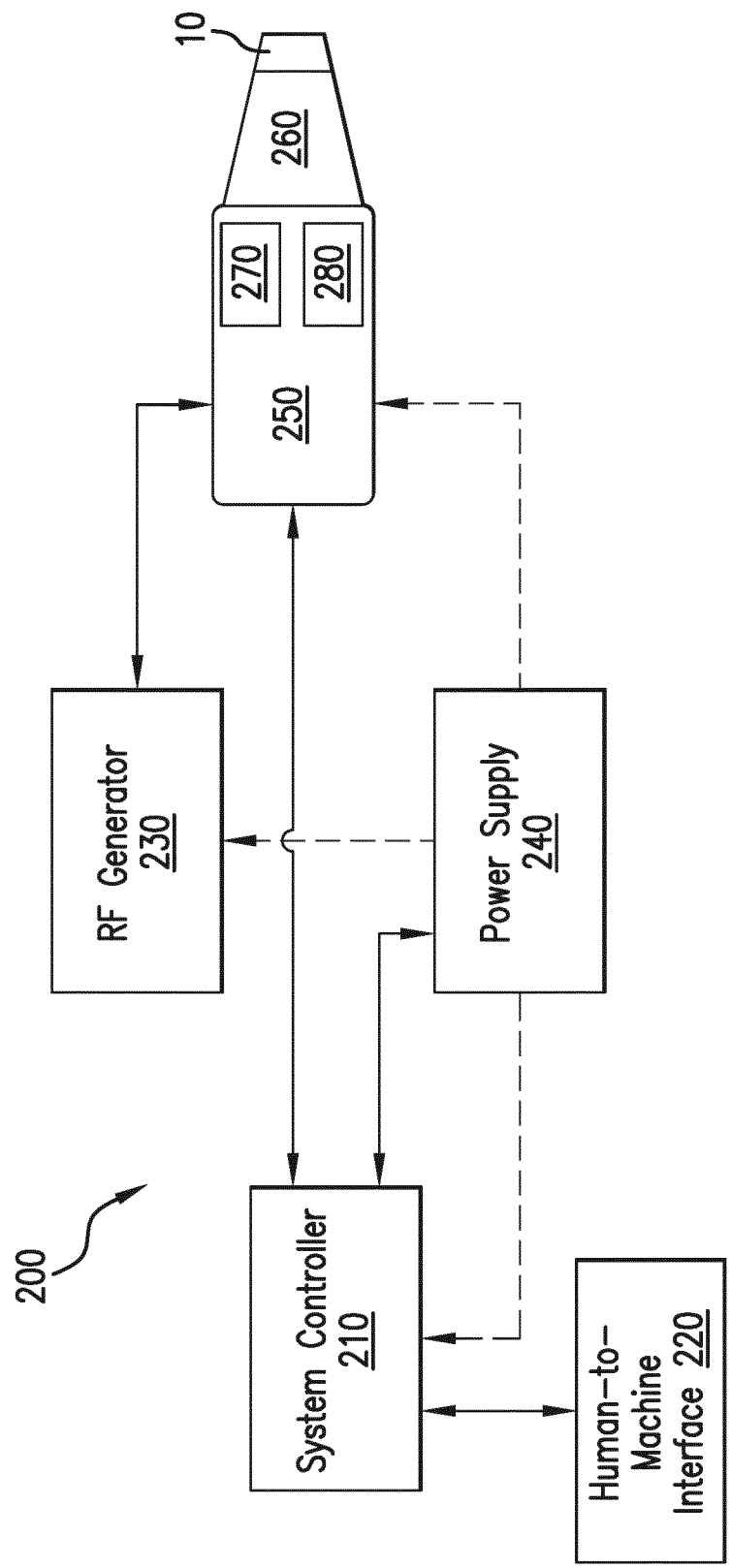
FIG. 1 is a block diagram of an example energy-based therapeutic device that is suitable for implementing aspects of the invention described herein.
Figure 2:
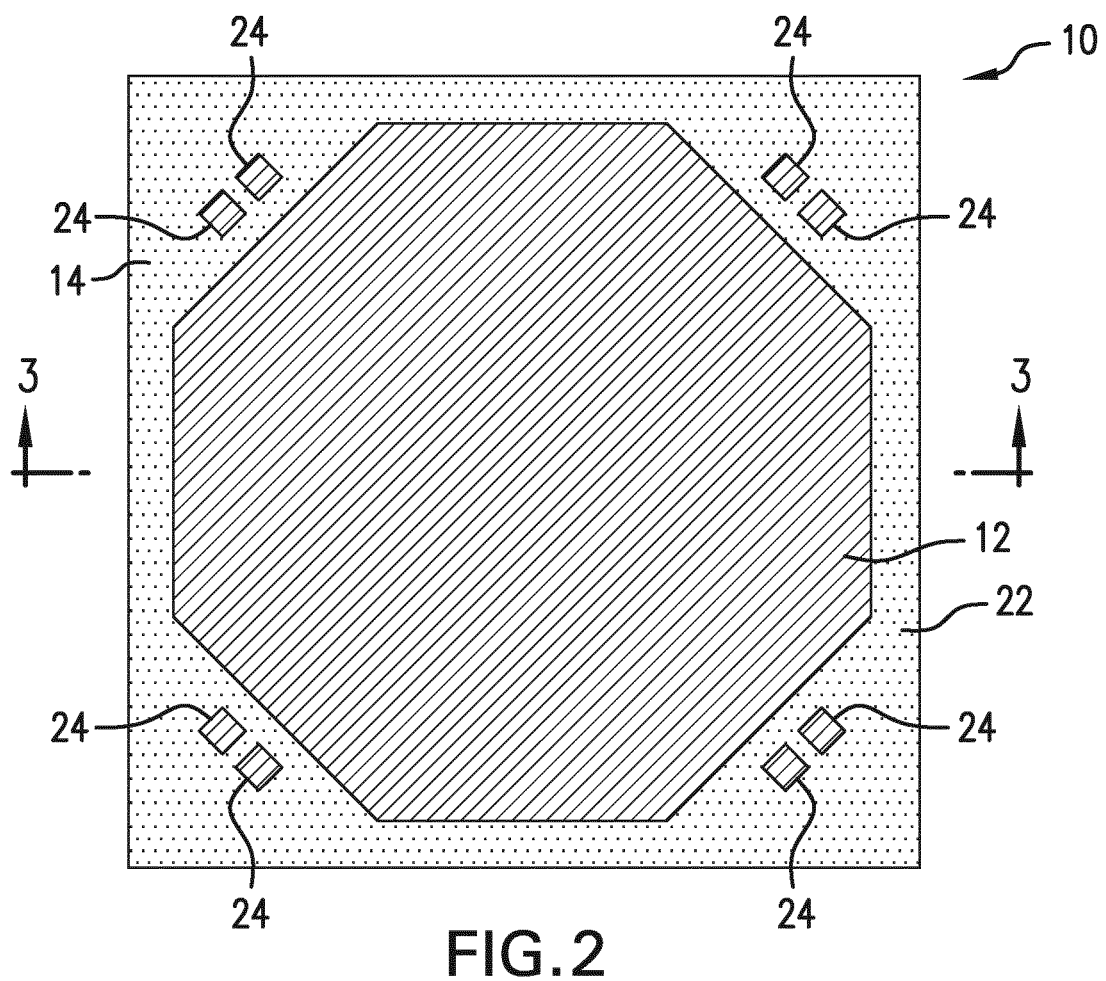
FIG. 2 is a front view of an applicator in accordance with embodiments of the invention.
Figure 3:
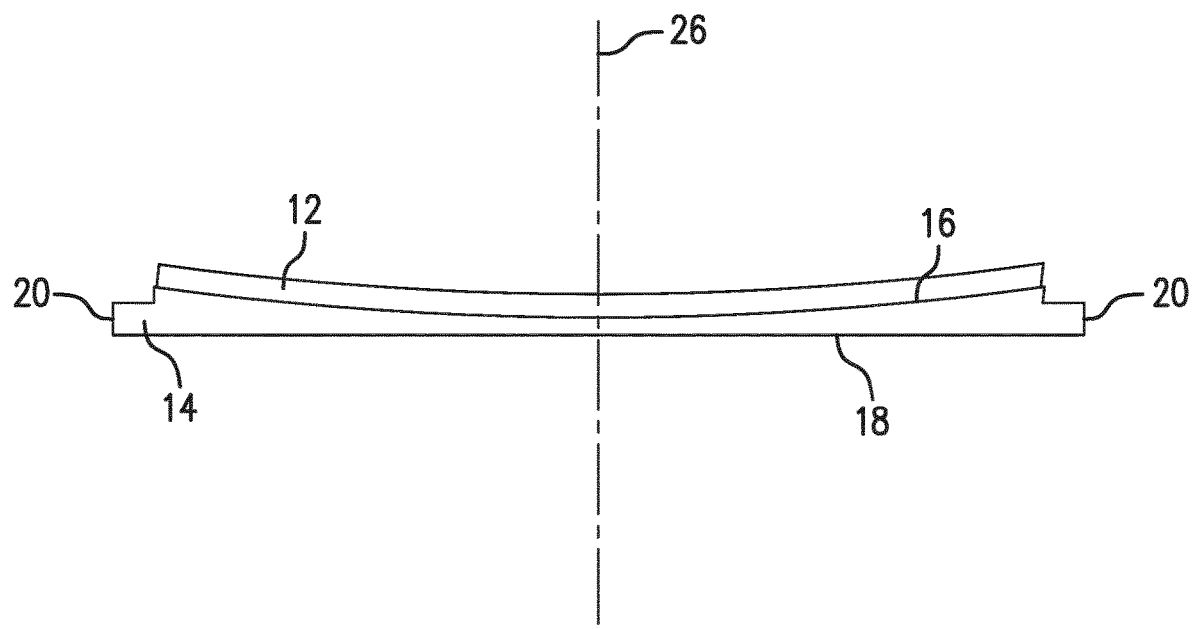
FIG. 3 is a cross-sectional view of the applicator of FIG. 2.

With reference to FIGS. 1-3 and in accordance with embodiments of the invention, an energy-based therapeutic device 200 includes a system controller 210, a human-to-machine interface ("HMI") 220, a high-frequency generator 230, a power supply 240, a handpiece 250, and a treatment tip 260. The system controller 210 is generally configured to control the operation and functionality of the device 200 by controlling the other components of the device 200, such as the high-frequency generator 230 and the power supply 240. The system controller 210 is a high-level hardware controller that enables the application of high-frequency energy (e.g., radio-frequency (RF) energy) to a treatment area of a patient for use in, for example, a transcutaneous dermatological treatment. Lower level hardware controllers located in the other components of the device 200 may manage component-level operations under the direction and coordination of the system controller 210.

In controlling and orchestrating the operation of the other components, the system controller 210 may also monitor status messages received from the lower-level hardware controllers and various operational parameters during a procedure applying high-frequency energy to the treatment area. Examples of such operational parameters include: the peak/average output power emitted from the treatment tip 260, the temperature at the treatment tip 260, the patient-applied mechanical force, current values of usage data for the treatment tip, and the like. The system controller 210 may disable the application of high-frequency energy to the treatment area if the operational parameters or the status messages from the lower-level hardware controllers indicate a fault condition. For example, if a current value of usage data for the treatment tip 260 exceeds a threshold value, the system controller 210 will disable the application of high-frequency energy to the treatment area.

The HMI 220 provides an interface between an operator (e.g., a clinician) and the device 200 for exchanging commands, requests, information, data, and the like, which enable the operator to interact with the functionalities provided by the device 200. In an embodiment, the HMI 220 may include a touch-sensitive touch screen that provides both an input interface and an output interface between the operator and the device 200. In an embodiment, the HMI 220 may include an audio interface, such as a microphone and/or speaker. In an embodiment, the HMI 220 may include physical input devices, such as buttons (e.g., push buttons, rocker buttons, or other buttons known in the art), dials, slider switches, joysticks, click wheels, a keyboard, a pointer device (e.g., a mouse), and the like. The high-frequency generator 230 is configured to generate high-frequency energy (e.g., RF energy) for driving the electrode 12 in the treatment tip 260 when enabled by the system controller 210 and in accordance with commands received from an operator via the HMI 220. In an embodiment, the high-frequency energy may be radio-frequency energy in a range from one (1) megahertz (MHz) to twenty (20) megahertz.

The power supply 240 is configured to deliver electrical power from an external power source (e.g., an alternating current ("AC") outlet) to the various components of the device 200. In an embodiment, the power supply 240 is configured to convert AC power obtained from an external power source into direct current ("DC") power for delivery to the various components. In an embodiment, the power supply 240 may be configured to provide electrical isolation between the external power source and the other components of the device 200.

The handpiece 250 is configured to couple the treatment tip 260 to the other components of the device 200 along the high-frequency energy propagation path. The handpiece 250 is connected to the device 200 via a flexible conduit enclosing conductors that electrically couple the handpiece 250 to the other components. The handpiece 250 may be smoothly contoured grip for gripping and handling by a clinician serving as the operator, which permits the handpiece 250 to be grasped by at least one hand of the clinician for manipulating the location of the handpiece 250 and treatment tip 260. During a therapeutic procedure, an operator positions the handpiece 250 (and thereby the treatment tip 260 and its applicator 10) proximate to a treatment area of a patient and in contact with the treatment area. After contacting the treatment area with a portion of the treatment tip 260, as subsequently described, the operator may instruct the device 200 to deliver high-frequency energy from the applicator 10 to the treatment area by interacting with controls disposed on an outward surface of the handpiece 250 and/or controls at the console. For example, the handpiece 250 may include controls that enable the operator to initiate/terminate high-frequency energy delivery to the treatment area and/or adjust an amount of high-frequency energy that is applied to the treatment area.

The treatment tip 260 couples with the handpiece 250 to deliver high-frequency energy generated by high-frequency generator 230 to a patient for therapeutic purposes. The treatment tip 260 includes an applicator 10 that is designed to deliver the high-frequency energy in a specific density to the patient during the therapeutic procedure. The treatment tip 260 may include a housing in which the applicator 10 is contained and may be configured so as to be releasably attached to the handpiece 250. Sensor data indicative of a temperature at the treatment tip 260 may be obtained using temperature sensors (e.g., thermistors) included in the treatment tip 260.

In an embodiment, at least a subset of the components forming the device 200 are contained within a console (or mechanical enclosure). For example, the console may contain the system controller 210, the high-frequency generator 230, and the power supply 240. In an embodiment, the handpiece 250 is physically coupled to the console via the flexible conduit enclosing conductors that electrically couple the handpiece 250 to the other components of the device 200. All or part of the HMI 220 may be disposed on an outward facing surface of the console.

A fluid delivery member 270 may be arranged inside the handpiece 250 and/or treatment tip 260. A supply of the coolant (e.g., a coolant canister) may be located at the console of the device 200 and coupled by tubing with the fluid delivery member 270. The fluid delivery member 270 may be configured to controllably deliver a spray or stream of a coolant to the applicator 10 in conjunction with a treatment procedure. The coolant may be triggered under the control of the system controller 210 to deliver the coolant spray or stream before, during, and/or after the delivery of the high-frequency energy from the applicator 10 to the patient's tissue.

A vibration device 280 may be arranged inside the handpiece 250 and/or the treatment tip 260. The vibration device 280 is configured to oscillate or vibrate the treatment tip 260 and the applicator 10 at a relatively low frequency relative to the handpiece 250 and the treatment area. In particular, the vibration device 280 causes the treatment tip 260 to oscillate or vibrate in a path along an axis that is normal or substantially normal to the treatment area with at least a portion of the treatment tip 260 in contact with the treatment area to transfer the vibration to the treatment area. Without intending to be bound by any particular theory, it is believed that such vibration may provide a pain control mechanism for the patient during a treatment procedure.

With reference to FIGS. 2 and 3, the applicator 10 includes an electrode 12 and a substrate 14 that provides mechanical support for the electrode 12. The substrate 14 includes a surface 16, a surface 18 that is opposite the surface 16, and outer edges 20 that are arranged between the surface 16 and the surface 18 and that extends about the perimeter of the substrate 14. The electrode 12 also includes outer edges 13 that are inset within the outer edges 20 of the substrate 14 such that the surface 16 of the substrate 14 is only partially covered by the electrode 12.

The substrate 14 may include a frame 22 that surrounds an area of the substrate 14 on which the electrode 12 is positioned. The electrode 12 and the frame 22 may be individual components or may be fashioned by molding or machining from a single material. Thus, the frame 22 and the electrode 12 may be composed of the same material or at least two different materials. The electrode 12 is inset inside the frame 22, and the portion of the surface 16 on the frame 22 may be recessed relative to the portion of the surface 16 covered by the electrode 12 and in a plane that is parallel to the plane of surface 18 such that the frame 22 has a uniform thickness in contrast with the area on which the electrode 12 is positioned.

The substrate 14 has a thickness given by the separation between the surfaces 16, 18. The thickness between the surface 16 and the surface 18 varies as a function of position relative to the outer edges 20 of the substrate 14. In particular and as best shown in FIG. 3, the substrate 14 may have a thickness that increases with increasing distance from an imaginary centerline 26 extending normal to the surfaces 16, 18. Such thickness increases need not be uniform from the centerline 26, but the increases in thickness on either side of the centerline 26 should be symmetric about the centerline 26. Exemplary non-linear profiles include torus profile or a profile that initially increases in thickness with increasing radial distance from the centerline 26 and, at a given radius defining an inflection point, begins to decrease in thickness with increasing radial distance from the centerline 26. In an embodiment, the surface 16 of the substrate 14 may be concave with a radius of curvature that provides the position-dependent thickness variation. In an embodiment, the thickness of the substrate 14 may be rotationally symmetric about the centerline 26 such that the position-dependent thickness variation is likewise rotationally symmetric about the centerline 26. In an embodiment, the thickness of the substrate 14 may lack rotational symmetry about the centerline 26 such that the position-dependent thickness variation likewise lacks rotational symmetry about the centerline 26. The surface 18 of the substrate 14 may be substantially planar and lack intentionally-formed concavity or convexity. The surface 18 may provide a reference plane for measuring the variation in thickness of the substrate 14.

Figure 4:
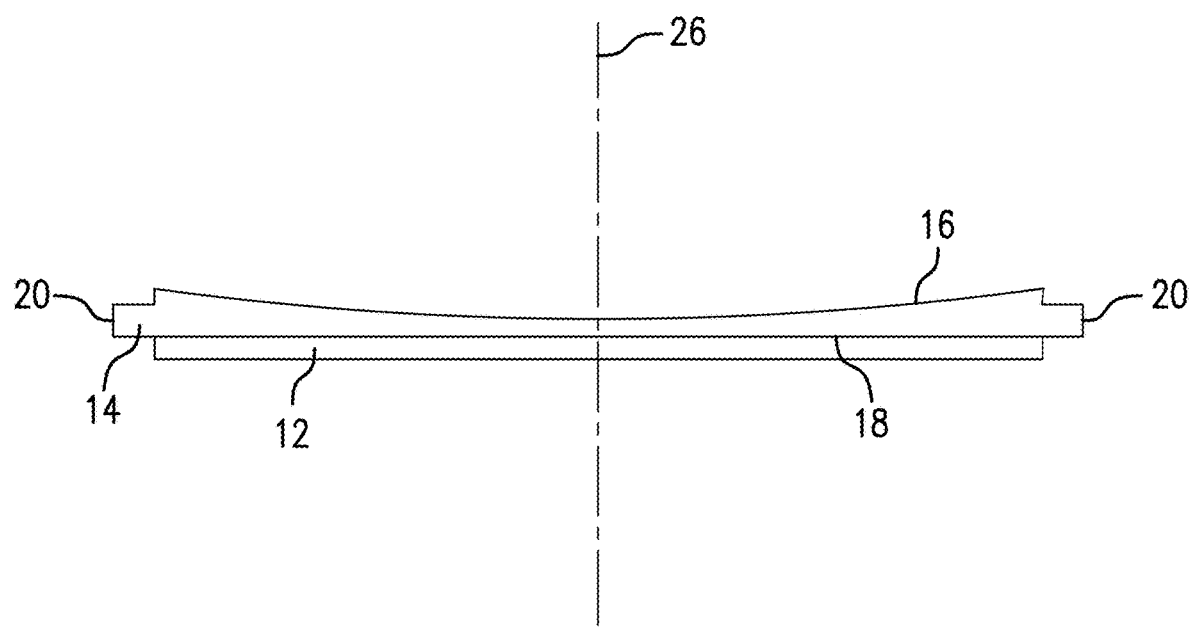
FIG. 4 is a cross-sectional view of the applicator of FIG. 2 in accordance with an alternative embodiment.

The applicator 10 may be positioned within the treatment tip 260 such that the substrate 14 is arranged between the electrode 12 and the tissue to be treated with high-frequency energy. In the representative embodiment, the electrode 12 may be positioned on the surface 16 of the substrate 14, and the surface 18 may be oriented to face outward from the treatment tip 260 and may be placed in direct contact with the patient's tissue. In an alternative embodiment and as shown in FIG. 4, the electrode 12 may be positioned on the surface 18, and the surface 16 may be oriented to face outward from the treatment tip 260 and may be placed in direct contact with the patient's tissue. The shape of the electrode 12 may differ from the representative shape shown in FIG. 2.

The electrode 12 may also be centered about the centerline 26 of the substrate 14. Alternatively, the center of the electrode 12 may be offset from the centerline 26 of the substrate 14. Connection points 24 may be included as additional metallization placed on the surface 16 including the electrode 12. For example, the connection points 24 may be pads used for attaching temperature sensors, such as thermistor packages, or other types of sensors.

In use during a treatment procedure, high-frequency energy is transferred from the electrode 12 through the thickness of the substrate 14 to treat tissue proximate to the treatment tip 260. The variation in the thickness of the substrate 14 may be effective in reducing the current density of the delivered high-frequency energy near the outer edges 13 of the electrode 12, which is typically greater than the current density inward from the outer edges 13 of the electrode 12. The reduction of the current density near the outer edges 20 of the substrate 14 may improve the uniformity of the delivery of high-frequency energy to the patient's tissue and, for that reason, the uniformity of tissue heating and treatment.

The substrate 14 may be composed of a ceramic material that is machined to provide the variation in thickness. Exemplary ceramic materials include, but are not limited to, aluminum nitride, alumina, yttria stabilized zirconia ("YTZP" or "YSZ"), or a combination thereof. In an embodiment, the ceramic material may be alumina.

In embodiments, the substrate 14 may be composed of a ceramic material having a thermal conductivity that is greater than a thermal conductivity of traditionally-employed polymeric substrates, such as polyimide, which improves the ability to conduct heat in comparison with traditionally-employed polymeric substrates. In some embodiments, the substrate 14 may be composed of a ceramic material having a thermal conductivity that is greater than 20 watts per meter-Kelvin. For instance, alumina has a thermal conductivity of 30 watts per meter-Kelvin and aluminum nitride has a thermal conductivity of 60 watts per meter-Kelvin, whereas polyimide has a thermal conductivity of 0.46 watts per meter-Kelvin.

The ability of the substrate 14 to efficiently transfer heat, which is directly related to thermal conductivity, may be beneficial in treatment procedures using the applicator 10 that rely on tissue cooling to protect superficial tissue and heat underlying tissue to a therapeutic temperature. A higher thermal conductivity may provide an improved cooling distribution and/or a more consistent surface temperature, in contrast with more localized hot spots often found when using traditional polyimide substrates. To that end, the applicator 10 may receive coolant delivered from a fluid delivery member 270 (FIG. 1) that is arranged inside the handpiece 250 and/or treatment tip 260. A supply of the coolant (e.g., a coolant canister) may be located at the console of the device 200. The fluid delivery member 270 may be configured to controllably deliver a spray or stream of a coolant to the applicator 10 in association with a treatment procedure. The coolant may be triggered under the control of the system controller 210 to deliver the coolant stream or spray before, during, and after the delivery of the high-frequency energy from the electrode 12 to the patient's tissue. Due to the temperature differential existing between the cooled applicator 10 and the contacted tissue that is heated by the delivered high-frequency energy, heat is conducted from the contacted tissue through the thickness of the substrate 14 and thereby extracted from the contacted tissue. Portions of the handpiece 150 and/or treatment tip 260 may provide a heat sink that dissipates the extracted heat to the surrounding environment. The heat removal cools the contacted tissue from the tissue surface inward, which compensates for heating proximate to the tissue surface and may thereby generate a reverse thermal gradient that extends from the tissue surface to a given depth into the tissue. The cooling and energy delivery may be balanced so as to not significantly interfere with tissue heating occurring over the tissue depths at which treatment is desired, while concurrently cooling the tissue between these tissue depths and the tissue surface at which heating to the treatment temperature is not desired.

In some embodiments, the substrate 14 may be composed of a ceramic material having a dielectric constant (i.e., permittivity) that is greater than eight (8) in a frequency range from one (1) megahertz (MHz) to twenty (20) megahertz. For instance, alumina has a dielectric constant of about ten (10) in a frequency range from 1 megahertz to 20 megahertz and aluminum nitride has a dielectric constant of about nine (9) in a frequency range from 1 megahertz to 20 megahertz, whereas polyimide has a lower dielectric constant of about 4.2 in the same frequency range. In some embodiments, the substrate 14 may be composed of a ceramic material having a dielectric loss tangent that is less than $1 \times 10^{-4}$ in a frequency range from 1 megahertz to 20 megahertz, whereas polyimide has a dielectric tangent loss of less than $5 \times 10^{-3}$ in this frequency range. In some embodiments, the ceramic material of the substrate 14 may possess more than one, or all, of these designated properties of thermal conductivity, dielectric constant, and dielectric loss tangent.

The electrode 12 may be composed of a conductor, such as copper or aluminum. The electrode 12 may be applied to the substrate 14 by, for example, lamination, vapor deposition, sputter deposition, or other methods known in the art, and may be patterned by photolithography and etching processes following application to define the outer edges 13 of the electrode 12 and the connection points 24 arranged about the outer edges 13 of the electrode 12. The electrode 12 may be contacted by, for example, pogo pins in the handpiece 250 or treatment tip 260 when the treatment tip 260 is coupled with the handpiece 250.

References herein to terms such as "vertical," "horizontal," and the like are made by way of example, and not by way of limitation, to establish a frame of reference. It is understood that various other frames of reference may be employed for describing the invention without departing from the spirit and scope of the invention. It is also understood that features of the invention are not necessarily shown to scale in the drawings. Furthermore, to the extent that the terms "composed of," "includes," "having," "has," "with," or variants thereof are used in either the detailed description or the claims, such terms are intended to be inclusive and open-ended in a manner similar to the term "comprising."

References herein to terms modified by language of approximation, such as "about", "approximately", and "substantially", are not to be limited to the precise value specified. The language of approximation may correspond to the precision of an instrument used to measure the value and, unless otherwise dependent on the precision of the instrument, may indicate +/−10% of the stated value(s).

A feature "connected" or "coupled" to or with another feature may be directly connected or coupled to or with the other feature or, instead, one or more intervening features may be present. A feature may be "directly connected" or "directly coupled" to or with another feature if intervening features are absent. A feature may be "indirectly connected" or "indirectly coupled" to or with another feature if at least one intervening feature is present. A feature "on" or "contacting" another feature may be directly on or in direct contact with the other feature or, instead, one or more intervening features may be present. A feature may be "directly on" or in "direct contact" with another feature if intervening features are absent. A feature may be "indirectly on" or in "indirect contact" with another feature if at least one intervening feature is present.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

While the invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. Thus, the invention in its broader aspects is therefore not limited to the specific details, representative apparatus and method, and illustrative example shown and described. Accordingly, departures may be made from such details without departing from the spirit or scope of applicants' general inventive concept.

What is claimed is:

1. An energy delivery device comprising:
   an applicator including an electrode and a substrate comprising a ceramic material, the substrate having a first surface, a second surface opposite to the first surface, and one or more outer edges between the first surface and the second surface, and the substrate having a thickness between the first surface and the second surface that varies as a function of position relative to the one or more outer edges,
   wherein the ceramic material is aluminum nitride having a dielectric constant of about 9 in a frequency range from 1 Megahertz to 20 Megahertz, the substrate has a centerline, the ceramic material of the substrate extends from the centerline to the one or more outer edges, and the thickness of the ceramic material of the substrate increases non-linearly with increasing distance from the centerline.

2. The energy delivery device of claim 1 wherein the first surface of the substrate has a concave shape with a radius of curvature.

3. The energy delivery device of claim 2 wherein the second surface of the substrate is planar.

4. The energy delivery device of claim 3 wherein the electrode is arranged on the second surface of the substrate.

5. The energy delivery device of claim 2 wherein the electrode is arranged on the first surface of the substrate.

6. The energy delivery device of claim 1 wherein the electrode is centered about the centerline of the substrate.

7. The energy delivery device of claim 1 further comprising:
   a treatment tip having a housing,
   wherein the applicator is arranged inside the housing.

8. The energy delivery device of claim 7 further comprising:
   a handpiece,
   wherein the treatment tip is configured to be releasably attached to the handpiece.

9. The energy delivery device of claim 1 wherein the ceramic material has a thermal conductivity that is greater than a thermal conductivity of polyimide.

10. The energy delivery device of claim 1 wherein the ceramic material has a thermal conductivity that is greater than 20 watts per meter-Kelvin.

11. The energy delivery device of claim 1 wherein the ceramic material has a dielectric loss tangent that is less than $1 \times 10^{-4}$ in a frequency range from 1 Megahertz to 20 Megahertz.

12. The energy delivery device of claim 1 wherein the thickness of the substrate is rotationally symmetric about the centerline.

13. A method of delivering high-frequency energy, the method comprising:
   transferring the high-frequency energy from an electrode through a substrate to treat tissue proximate to the electrode with a current density that is smaller near one or more outer edges of the electrode than inward from the one or more outer edges of the electrode, wherein the substrate has a thickness that varies as a function of position relative to one or more outer edges of the substrate, the substrate has a centerline, the substrate comprises a ceramic material, the ceramic material is aluminum oxide having a dielectric constant of about 10 in a frequency range from 1 Megahertz to 20 Megahertz or aluminum nitride having a dielectric constant of about 9 in a frequency range from 1 Megahertz to 20 Megahertz, the ceramic material of the substrate extends from the centerline to the one or more outer edges of the substrate, and the thickness of the ceramic material of the substrate increases non-linearly with increasing distance from the centerline.

14. An energy delivery device comprising:
an applicator including an electrode and a substrate comprising a ceramic material, the substrate having a first surface, a second surface opposite to the first surface, and one or more outer edges between the first surface and the second surface, and the substrate having a thickness between the first surface and the second surface that varies as a function of position relative to the one or more outer edges,
wherein the ceramic material is aluminum oxide having a dielectric constant of about 10 in a frequency range from 1 Megahertz to 20 Megahertz, the substrate has a centerline, the ceramic material of the substrate extends from the centerline to the one or more outer edges, and the thickness of the ceramic material of the substrate increases non-linearly with increasing distance from the centerline.

15. The energy delivery device of claim 14 wherein the first surface of the substrate has a concave shape with a radius of curvature.

16. The energy delivery device of claim 15 wherein the second surface of the substrate is planar.

17. The energy delivery device of claim 16 wherein the electrode is arranged on the second surface of the substrate.

18. The energy delivery device of claim 15 wherein the electrode is arranged on the first surface of the substrate.

19. The energy delivery device of claim 14 wherein the ceramic material has a thermal conductivity that is greater than 20 watts per meter-Kelvin.

20. The energy delivery device of claim 14 wherein the ceramic material has a dielectric loss tangent that is less than $1 \times 10^{-4}$ in a frequency range from 1 Megahertz to 20 Megahertz.

21. The energy delivery device of claim 14 wherein the electrode is centered about the centerline of the substrate.

22. The energy delivery device of claim 14 further comprising:
a treatment tip having a housing,
wherein the applicator is arranged inside the housing.

23. The energy delivery device of claim 22 further comprising:
a handpiece,
wherein the treatment tip is configured to be releasably attached to the handpiece.

24. The energy delivery device of claim 14 wherein the thickness of the substrate is rotationally symmetric about the centerline.

* * * * *

UNITED STATES PATENT AND TRADEMARK OFFICE
CERTIFICATE OF CORRECTION

PATENT NO. : 12,251,152 B2
APPLICATION NO. : 17/299578
DATED : March 18, 2025
INVENTOR(S) : Frederick Jay Bennett and Craig Robert Bockenstedt It is certified that error appears in the above-identified patent and that said Letters Patent is hereby corrected as shown below:

On the Title Page

Item (57) ABSTRACT reads:
"Structures for a bidirectional switch and methods of forming such structures. A substrate contact is formed in a trench defined in a substrate. A substrate includes a trench and a substrate contact in the trench. A bidirectional switch, which is on the substrate, includes a first source/drain electrode, a second source/drain electrode, an extension region between the first source/drain electrode and the second source/drain electrode, and a gate structure. A substrate-bias switch, which is on the substrate, includes a gate structure, a first source/drain electrode coupled to the substrate contact, a second source/drain electrode coupled to the first source/drain electrode of the bidirectional switch, and an extension region laterally between the gate structure and the first source/drain electrode."

It should read:
--Energy delivery devices and methods of treating tissue with high-frequency energy. The energy delivery device may include an applicator having an electrode and a substrate. The substrate may be composed of a ceramic material and may have a surface characterized by a variable thickness, such as a concave surface.--

Signed and Sealed this
Tenth Day of June, 2025

Coke Morgan Stewart
*Acting Director of the United States Patent and Trademark Office*